United States Patent
Fuller

[19]

[11] Patent Number: 5,879,665
[45] Date of Patent: Mar. 9, 1999

[54] COMPOSITION FOR CAUSING SKIN LIGHTENING

[75] Inventor: Bryan B. Fuller, Edmond, Okla.

[73] Assignee: The Board of Regents of The University of Oklahoma, Norman, Okla.

[21] Appl. No.: 936,977

[22] Filed: Sep. 25, 1997

[51] Int. Cl.$^6$ ................................................. A61K 7/42
[52] U.S. Cl. ........................... 424/62; 424/195.1; 424/59
[58] Field of Search ....................... 424/62, 195.1, 424/59

[56] References Cited

U.S. PATENT DOCUMENTS

| | | | |
|---|---|---|---|
| 3,022,311 | 2/1962 | Weisenborn et al. | 260/287 |
| 4,925,943 | 5/1990 | Kanmacher et al. | 546/149 |
| 5,082,665 | 1/1992 | Verny | 424/464 |
| 5,145,852 | 9/1992 | Virag | 514/253 |
| 5,164,182 | 11/1992 | Meybeck et al. | 424/195.1 |
| 5,262,153 | 11/1993 | Mishima et al. | 424/62 |
| 5,279,834 | 1/1994 | Meybeck | 424/450 |
| 5,350,756 | 9/1994 | Smith | 514/289 |
| 5,462,856 | 10/1995 | Lerner et al. | 435/7.21 |
| 5,529,769 | 6/1996 | Cho et al. | 424/74 |
| 5,565,466 | 10/1996 | Gioco et al. | 514/280 |
| 5,609,875 | 3/1997 | Hadas | 424/195.1 |
| 5,705,170 | 1/1998 | Kong et al. | 424/401 |

OTHER PUBLICATIONS

Yokoyama et al., *Chemical Abstracts*, vol. 123, #296253, 1994.

F. Morishita, "Response of the Melanophores of the Medaka, *Oryzias latipes*, to Adrenergic Drugs: Evidence for Involvement of Alpha$_2$ Adrenergic Receptors Mediating Melanin Aggregation", *Comp. Biochem. Physiol.*, 88C(1):69–74, 1987.

*Primary Examiner*—Thurman K. Page
*Assistant Examiner*—J. Spear
*Attorney, Agent, or Firm*—Dunlap, Codding & Rogers, P.C.

[57] ABSTRACT

A method and composition for the topical application of a yohimbine or derivative or stereoisomer thereof, or effective $\alpha_2$-antagonists, skin for inhibiting melanogenesis in the skin leading to skin lightening. The yohimbine may be provided as a natural extract, for example, as an extract of Johimbe bark.

15 Claims, 8 Drawing Sheets

COMPOSITION FOR CAUSING SKIN LIGHTENING

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND

The present invention generally relates to depigmenting or skin-lightening compositions for topical application on a subject's skin and methods of their use.

Skin color in humans arises from a complex series of cellular processes which are carried out within a unique population of cells called melanocytes. Melanocytes are located in the lower part of the epidermis, and their function is to synthesize a brown pigment, melanin, which protects the body from the damaging effects of ultraviolet radiation. Melanin is deposited in melanosomes, which are vesicles found within the melanocytes. The melanosomes are extruded from the melanocytes and carried to the surface of the skin by keratinocytes, which internalize the melanin containing melanosomes. The darkness of the color observed in the skin is proportionate to the amount of melanin synthesized by melanocytes and transferred to the keratinocytes. In some cases, it is desirable to reduce or inhibit melanogenesis, for example, to cause skin lightening, to eliminate "age spots" or to reduce hyperactive melanocytes.

SUMMARY OF THE INVENTION

The objective of the present invention is to provide a method and composition for topical application to the skin for inhibiting melanogenesis thereby causing skin lightening.

In a preferred version the present invention comprises a composition of matter comprising an amount of an active agent comprising yohimbine or an effective derivative, stereoisomer or salt thereof effective in decreasing levels of melanin in a human melanocyte. The composition also comprises an effective amount of a pharmaceutically acceptable topical carrier which is capable of delivering the yohimbine or stereoisomer, derivative or salt thereof to the melanocyte-containing skin layer under in vivo conditions. The active agent may be provided as a natural extract, for example, as an extract of Johimbe tree bark.

The present invention also comprises a method for decreasing pigmentation or promoting lightening of the skin of a subject. The subject's skin is treated with a depigmenting composition comprising a yohimbine effective in decreasing the amount of melanin in a human melanocyte, and a pharmaceutically acceptable topical carrier as previously described. Such a method of application may further comprise a sunscreen composition to at least partially shield the subject's skin from ultraviolet radiation.

More particularly, the present invention contemplates a composition, and method of using such, which is effective in inhibiting melanogenesis in human skin, the composition comprising an effective amount of a yohimbine capable of decreasing levels of melanin in melanocytes in human skin.

DETAILED DESCRIPTION OF THE INVENTION

Figure 1:
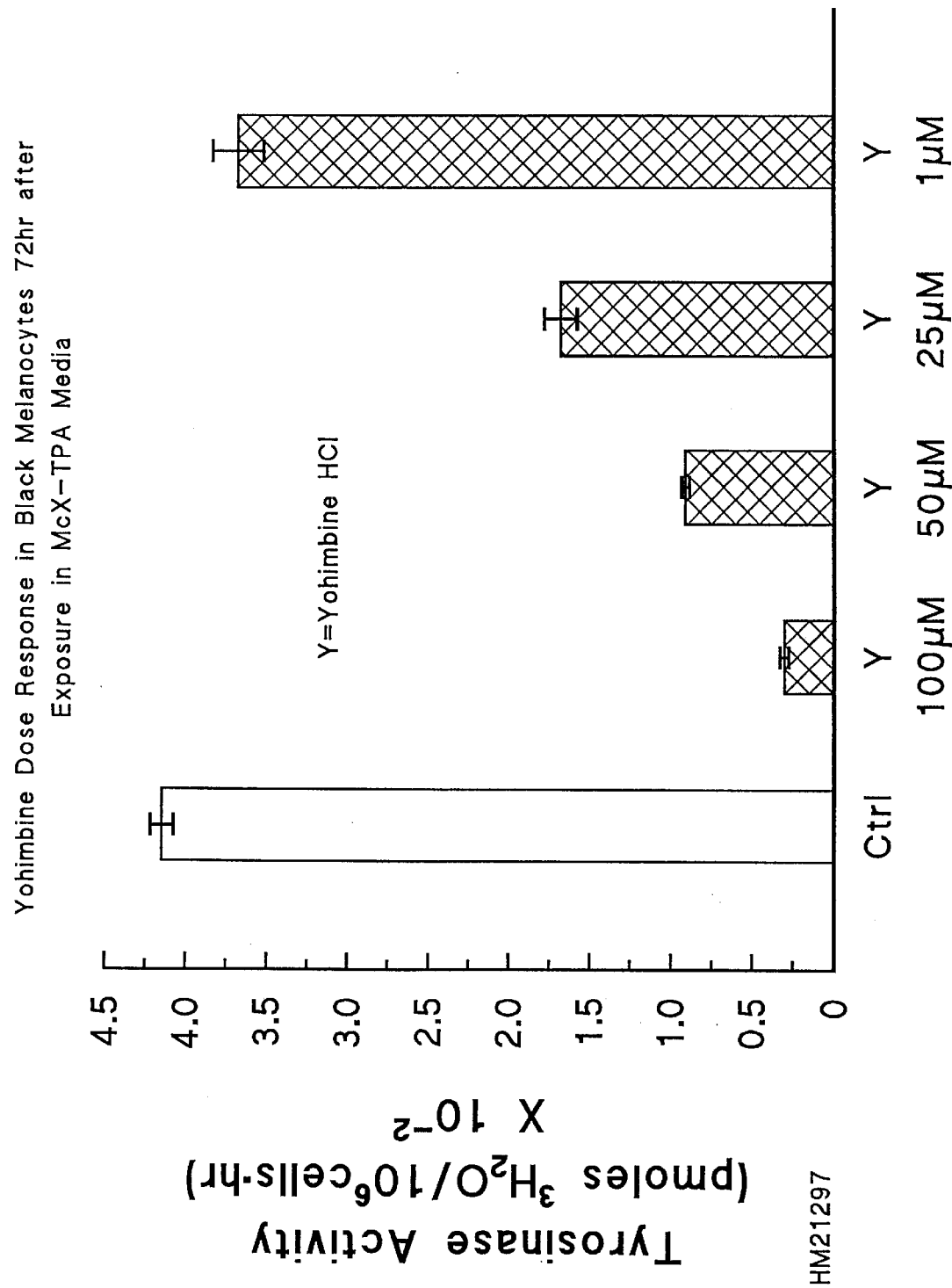
FIG. 1 is a graph showing the dose response effect of yohimbine on tyrosinase activity in melanocytes.

The present invention is directed to compositions and methods which decrease melanogenesis in the skin of subjects. "Subjects" as used herein mean mammals, and, more preferably, humans.

The present invention comprises compositions comprising an effective amount of one or more yohimbines or active agents (e.g., $\alpha_2$-antagonists) capable of decreasing the amount of melanin in a melanocyte (also referred to herein as "melanin-decreasing agents") and preferably, in a human melanocyte, and more preferably, in melanocytes in intact human skin. The melanin-decreasing agent may function in any of the various ways that are believed to decrease the amount of melanin produced within the skin, for example, by decreasing cAMP (cyclic AMP) or derivatives of cAMP which function as cAMP in the melanocyte; by promoting phosphodiesterase; or by decreasing tyrosinase activity. The present invention, as noted above, additionally comprises all $\alpha_2$-antagonists which are effective in accordance with the present invention wherein the melanogenesis in melanocytes is inhibited leading to a lightening of the skin.

It is Applicant's unique discovery therefore, described further herein, that yohimbines, and certain other agents (such as certain $\alpha_2$-antagonists) are effective in decreasing melanin production in melanocytes thereby reducing skin pigmentation resulting in skin lightening.

More particularly, the present invention contemplates a composition, and method of using such, which is effective in inhibiting melanogenesis in human skin. The composition comprises an effective amount of a yohimbine capable of decreasing levels of melanin in a human melanocyte. Where used herein the term yohimbine is meant to include stereoisomers, salts, and derivatives of yohimbine which are also effective in depigmentation. Examples are rauwolscine ($\alpha$-yohimbine), allo-yohimbine, and corynanthine (rauhimbine).

The yohimbine or other active agent as described herein may comprise from about 0.01 $\mu$M to about 10 mM of the composition, or from about $10^{-4}$ to about 1% by weight of the composition. More preferably, the active agent comprises from about $10^{-4}$ to about 0.1% by weight of the composition. More preferably, the active agent yohimbine comprises from about $10^{-3}$% to about 0.1% by weight of the composition. In one version of the invention, the yohimbine, or yohimbine derivative or stereoisomer may be provided as an extract from the bark of the Johimbe (Yohimbe) tree (*Coryuanthe johimbe,* or related trees) or from any other natural source known to contain yohimbine or said derivatives or stereoisomers such as (e.g., *Rauwolfia serpentina* root). Methods of preparing such an extract are known to those of ordinary skill, and may be prepared by homogenizing the bark in ethanol, then centrifuging the homogenate to remove suspended particles. The be combined with a carrier for topical application. A more detailed example of an extraction process is described below.

The composition may further comprise a sunscreening agent for inhibiting the melanogenesis induced by ultraviolet light. Such screening agents, or sunscreens, are well known to those of ordinary skill in the art. As noted above, the composition comprises a pharmaceutically acceptable topical carrier capable of delivering the active agent to the skin layer containing melanocytes under in vivo conditions.

The melanin-decreasing agent (i.e., active agent) is present in the compositions of the present invention in any effective amount. An "effective amount" of the melanin-decreasing agent is an amount which decreases melanogenesis in the treated area of the subject. This amount may vary with, among other things, the identity of melanin-decreasing agent and carrier, the subject's skin color and condition, and the degree of depigmentation (i.e., lightening) sought.

The composition of matter of the present invention is preferably applied directly to the skin of the individual seeking lightening of the skin. The treated area can be the entire skin surface of the subject or only those areas in need of lightening or depigmentation. Application of the composition must be repeated periodically to maintain the lightened condition of the skin.

As noted above, the compositions of matter of the present invention preferably additionally comprises an effective amount of a pharmaceutically acceptable topical carrier capable of delivering the melanin-decreasing agent to the melanocyte skin layer under in vivo conditions. The carrier may comprise any solution, suspension, emulsion or any other form which is capable of delivering the agent to the melanocyte skin layer under in vivo conditions. "Capable of delivery", as used herein, means that the carrier should aid the agent in crossing the stratum corneum and successive cell layers found epidermal to the melanocyte, and/or aids the agent in reaching the layer of cells containing melanocytes. Preferably, the carrier should not substantially interact with the agent so that the agent may perform its function as described herein.

The identity and quantity of the carrier will depend on the identity of the melanin-decreasing agent used in the composition of the present invention. However, in may instances, the carrier will represent from about 50% to about 99% of the composition. Preferably the carrier will comprise an alcohol. Alternatively, the carrier may be liposomes or hydrated lipidic lamellar phases, such as are well-known to those of ordinary skill in the art.

Preferred formulations of the carrier contain an alcohol (e.g., methanol, ethanol or isopropanol), and a thickener such as propylene glycol, polyethylene glycol (PEG) or carbopol and a penetration enhancer such as transcutol.

Specific examples of preferred carrier formulations into which the active agent is disposed are:

(1) 30% propylene glycol (PG): 70% ethanol;
(2) 30% PG: 1.0–2.5% oleic acid or oleyl alcohol: ethanol (QS);
(3) 10–25% ethoxydiglycol: 0–2.5% oleic acid or oleyl alcohol: 0–5% hydroxypropyl cellulose: ethanol (QS);
(4) 10–50% methylpyrrolidone: 0–20% ethoxydiglycol: 0–2.5% oleic acid or oleyl alcohol: 0–5% hydroxypropyl cellulose: ethanol (QS).

The formulations described herein could be topically applied in a number of ways to achieve penetration of the active substance through the skin leading to skin lightening. The composition of matter is preferably in a gel, lotion or solution form which may be manually rubbed on the skin. Other means of application are acceptable such as aerosol sprays or the use of an applicator bottle. Typically, the formulation will be applied over the skin in a dosage of 0.3 to 1 ml/100 cm$^2$. This formulation may be applied at a frequency of every one to two to six to eight to 12 hours to the areas where lightening is desired. As defined herein the term dosage means the amount and frequency of application of the formulation to the skin. A formulation may comprise a film former such as polyvinyl pyrrolidone or polymethylpyrrolidone. Furthermore, a penetration enhancer (such as transcutol (ethoxydiglycol)) that allows the composition to accumulate in the stratum corneum could be used.

Additional ingredients may also be included in the compositions of the present invention. Penetration enhancers, when present, will preferably comprise from about 0.5–25% weight to the solvent mixture and more preferably will comprise from 1.0–20% by weight. Transcutol is a preferred penetration enhancer, but other known enhancers such as Azone (laurocapram), calcium thioglycolate, alkanecarboxylic acids, liposomes, DMSO, polar lipids, dimethylformamide, N-methyl-2-pyrrolidone, oleic acid, oleyl alcohol, decylmethyl sulfoxide, and propylene glycol are also enabled herein and may comprise portions of the formulation. Other possible penetration enhancers which may be used in any of the compositions described herein include: lauryl alcohol, dibutyl sebacate, diethyleneglycol oleate, diethyl sebacate, diethyl succinate, diisopropyl sebacate, dioctyl adipate, dioctyl azelate, dioctyl sebacate, ethyl acetate, glycerol monolaurate, glycerol monooleate, isopropyl isostearate, isopropyl myristate, isopropyl palmitate, sucrose monolaurate, sucrose monooleate, lactic acid, lauric acid, linoleic acid, linolenic acid, vaccenic acid, EO-2oleyl ether, EO-5-oleyl ether, EO-10-oleyl ether, N-methyl-2-pyrrolidone, pyrrolidone/carboxylic acid combinations, ethanol, polyethylene glycol, Tween 20 and Tween 80.

The composition may further comprise one or more hydrotropic substances which function to increase disorder in the lamellar liquid crystalline structure of the stratum corneum and thus allow increased transdermal transport. Examples of such hydrotropes are isopropyl alcohol, propylene glycol and sodium xylene sulfonate.

Applicants further contemplate that the formulations may comprise combinations of effective skin lighteners.

The compositions of the present invention may further comprise other cosmetically and therapeutically acceptable carriers or vehicles containing other solvents, moisturizers, humectants, oils, emulsifiers, thickeners, thinners, surface active agents, fragrances, preservatives, antioxidants, vitamins and minerals.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Methodology

Organ Culture System

Use of a human organ culture emulates the human skin in vivo and has permitted the adequate evaluation and development of the compositions and methods of treatment of the present invention. The human organ culture of the present invention employs a viable foreskin. "Viable" means there has been no substantial morphological change in the foreskin after surgical removal. Viability may be determined by changes in tissue ultrastructure determined through histochemical staining and/or dopa reaction staining, techniques which permit monitoring of any changes in the tissue ultrastructure.

The foreskins may be obtained by circumcising male neonates by standard surgical procedures. After surgical removal, the foreskin is preferably prepared for the organ culture by injection intradermally with the medium described hereafter. This swells the mucous membrane and allows for the removal of the membrane thereby allowing adequate nutrient flow to the foreskin through the dermis.

The foreskin comprises an epidermis which is normally exposed to the environment and a dermis opposing the epidermis. After surgical removal and preparation for the organ culture, the dermis, which is normally supplied nutrients by the body, is exposed to the environment. In order to maintain the viability of the foreskin, a nutrient medium supplies nutrients to the foreskin through the dermis as described hereafter.

The nutrient medium is any composition which maintains the viability of the foreskin. Preferably, the nutrient medium has a liquid phase such as a solution, suspension or emulsion. A portion of the medium may be obtained commercially, such as Iscove's modified Dulbecco's medium (IMDM), Ham's nutrient mixture F-10 medium, Minimum essential media (MEM), RPMI media 1630 or 1640, Dulbecco's Modified Eagle Media (D-MEM) or Media 199 all of which are manufactured by Gibco Laboratories of Grand Island, N.Y. as well as other companies, the specification sheets of which are hereby incorporated by reference. Additionally the medium comprises about 10% to about 30% horse serum and about 2% to about 10% fetal bovine serum; such serums may be purchased from Hyclone Lab Inc., of Logan, Utah, for example. If necessary, an alkalizer such as sodium bicarbonate may be added until the medium achieves a preferred pH, preferably about a physiological pH. Antibiotics such as penicillin and/or streptomycin may also be added for microbial control.

If transportation of the foreskin is necessary after surgical removal, the foreskin is immediately placed on an absorbent support saturated with the nutrient medium. In order to maintain the viability of the foreskin, the foreskin is disposed in the medium within about 3–4 hours after surgical removal. The position of the foreskin in the medium should be that the dermis contacts the medium and the epidermis is not substantially contacted by the medium.

A complete description of the foreskin organ culture system is found in U.S. Pat. No. 5,540,914 which is hereby incorporated herein by reference in its entirety.

Once the foreskin is disposed in the organ culture system as described herein, the organ culture system is incubated during the length of observation of the foreskin, for example, for 27–72 hours. Preferably the medium is changed daily, since nutrients may be depleted over time, and the incubation causes degradation of medium components.

In preparing the human organ culture system described herein, the foreskin is surgically removed, prepared and disposed in the organ culture system as described herein. Before positioning the foreskin in the system, the foreskin should be observed to determine the amount and/or the condition of the biological factor under study to obtain a baseline measurement. After treatment of the foreskin with an agent, the biological factor is again observed for a post-treatment measurement to be compared to the baseline measurement. For example, if the amount of tyrosinase in the foreskin is under study, the amount of tyrosinase is determined as a baseline measurement prior to application of the agent to the foreskin.

If the foreskin is to be treated with an agent under study, the agent can be added to the nutrient medium so that it comes into contact with the foreskin through the medium. Alternatively, the agent can be placed directly upon the epidermis of the foreskin. The treatment time will depend on the results sought, the identity of the agent under study, the time over which the foreskin can remain viable, and other variables.

After the foreskin has been treated with the agent under study, the foreskin may be observed and/or tested in any manner which will determine the differences in the foreskin from the observation and/or tests on the untreated foreskin. For example, the activity of tyrosinase may be measured as described herein and correlated to a decrease in melanogenesis; the rate of DNA synthesis can be measured by $^3$H-thymidine uptake and compared to controls; or the increase or decrease in the synthesis of proteins and/or RNA can be measured by determining the rate of incorporation of [$^3$H] leucine (protein) or [$^3$H] uridine (RNA) into acid-precipitating material. Alternatively, histological sections of the treated foreskin can be assessed microscopically as described elsewhere herein.

Preparation of Human Foreskin and Organ Culture

At the time of surgical removal, human foreskins were placed on sterile gauze saturated with sterile IMDM medium (Iscove's modified Dulbecco's medium purchased from Irvine Scientific of Santa Ana, Calif.) for transportation from the Hospital nursery to the laboratory. The tissues were rinsed in sterile IMDM medium containing 500 U/ml penicillin and 500 μg/ml of streptomycin for 5 minutes. Under sterile conditions, an intradermal injection of medium was performed from the dermal side prior to dissection of the mucous membrane and lower dermis by scissors to make the thickness of skins equal. The foreskins were then cut into approximately 3 mm×3 mm squares and either frozen at −75° C. or placed in organ culture as described below.

The organ culture medium was prepared from IMDM with glutamine supplemented with 20% horse serum, 5% fetal bovine serum, 100 U/ml penicillin, 100 μg/ml streptomycin and 3 mg/ml sodium bicarbonate. The serums were obtained from Hyclone Lab. Inc. of Logan Utah. Culture units were prepared by placing sterilized filters (AP20 025 00, Millipore) over sterilized support screens (25 cm Swinnex filter support screens, Millipore) in the wells of 6-well tissue culture plates (Falcon 3046) with medium added to the wells such that the skin support screens floated and the filter absorbed the medium from beneath. The tissue samples were placed, epidermis up, on top of the saturated filters and incubated at 37° C. in a 5% $CO_2$ humidified atmosphere. The medium was changed everyday. Harvested cultures were frozen at −75° C.

For histological study (light microscopy), thawed samples of fresh tissue and explants were mounted in OCT compound (ICN Immuno Biologicals, Lisle, Ill.) and frozen by liquid nitrogen. Cryostat sections (6 μm thick) were fixed in 2% formaldehyde for 2 hours at 40° C., and then stained either with hematoxylin and eosin or subjected to dopa staining. The dopa reactions were carried out by incubation in two changes of 0.1% L-dopa solution buffered to pH 7.4 in 0.1M sodium phosphate buffer for 4 hours at 37° C.

Determination of Tyrosinase Activity

Tyrosinase activity in human skin organ cultures was determined by measuring the tyrosine hydroxylase activity of the enzyme. The assay measures the production of $^3H_2O$ during the conversion of [$^3H$]tyrosine to L-DOPA. Weighed skin preparations were incubated in 0.3 ml of a reaction mixture containing 0.01 mM of L-tyrosine, 5–6 uCi/ml of [$^3H$]tyrosine and 0.1 mM L-DOPA in 0.1 M of pH 6.8 phosphate buffer for 4 hours at 37° C. To terminate the reaction, 1 ml of phosphate buffer was added, the tubes vortexed, and 0.4 ml aliquots removed in triplicate and mixed with an equal volume of Norit SG activated charcoal (10% w/v, in 0.1N HCl). Following centrifugation at 2000xg for 10 min, the supernatants (0.5 ml) were placed in scintillation vials, scintillation fluid added, and vials counted in a TM Analytic 6895 scintillation counter equipped with a DPM processor.

Melanocyte Bioassay

The normal human melanocyte cell strains used in this study were derived from foreskins of either neonates or from 2–6 year old black or white males. Human melanocyte cultures were grown in Ham's F-10 nutrient medium supplemented with 10% horse serum, 5% fetal bovine serum (FBS), 32 nM TPA (12-O-tetradecanoylphorbol 13-acetate), penicillin (100 units/ml), and streptomycin (100 μg/ml).

To determine tyrosinase activity in situ in human melanocyte cultures, the tyrosine hydroxylase activity of the enzyme was determined. Cells were seeded into 60-mm culture dishes at $2 \times 10^5$ cells/dish and allowed to attach overnight. The medium was then exchanged with a growth medium comprising Ham's F-10 nutrient medium +10% FBS+2 μg/ml Bovine Pituitary Extract (BPE)+2 ng/ml of Fibroblast growth factor (FGF), supplemented with 1 μCi/ml of [$^3H$] tyrosine (L-ring-3,5-$^3H$] -tyrosine, DuPont New England Nuclear), and with prostaglandin, where indicated. Cells were grown in labeled medium for 72 hours, (unless otherwise indicated) and at this time, the medium was removed and assayed for the presence of $^3H_2O$ using the charcoal absorption method of Pomerantz. Tyrosinase activity in cell homogenates was determined by sonicating cell pellets in 0.1-M sodium phosphate buffer (pH 6.8) and then incubating 50-μl aliquots in 0.5 ml of a reaction mixture containing 0.1-mM tyrosine, 2 μCi/ml of [$^3H$]tyrosine, 0.1-mM L-DOPA (dihydroxyphenylalanine), and 0.1 mM PMSF (phenylmethylsulfonyl fluoride) at 37° C. for 2 hours. Reactions were terminated by the addition of 1 ml of charcoal (10% w/v in 0.1-N HCl). Samples were centrifuged, and the supernatants removed for determination of the amount of $^3H_2O$ produced.

The amount of melanin in melanocytes was determined by incubating cell pellets in 2 ml of 1-N NaOH for 48 hours at 37° C. and then measuring the solubilized melanin at 400 nm.

Results

The effects of yohimbine, its stereoisomers and several other compounds on depigmentation in melanocytes and in cultured foreskin are shown in FIGS. 1–8. Melanocytes and foreskins were cultured as described above.

The effects of yohimbine HCl on tyrosinase activity in black melanocytes (strain B415) after a 72 hour incubation period in McX-TPA media are shown in FIG. 1. The results demonstrate a dose response wherein 100 μM yohimbine HCl strongly inhibits melanogenesis in black melanocytes while the effect progressively decreases until, at a concentration of 1 μM, the inhibitory effect has virtually disappeared.

Figure 2:
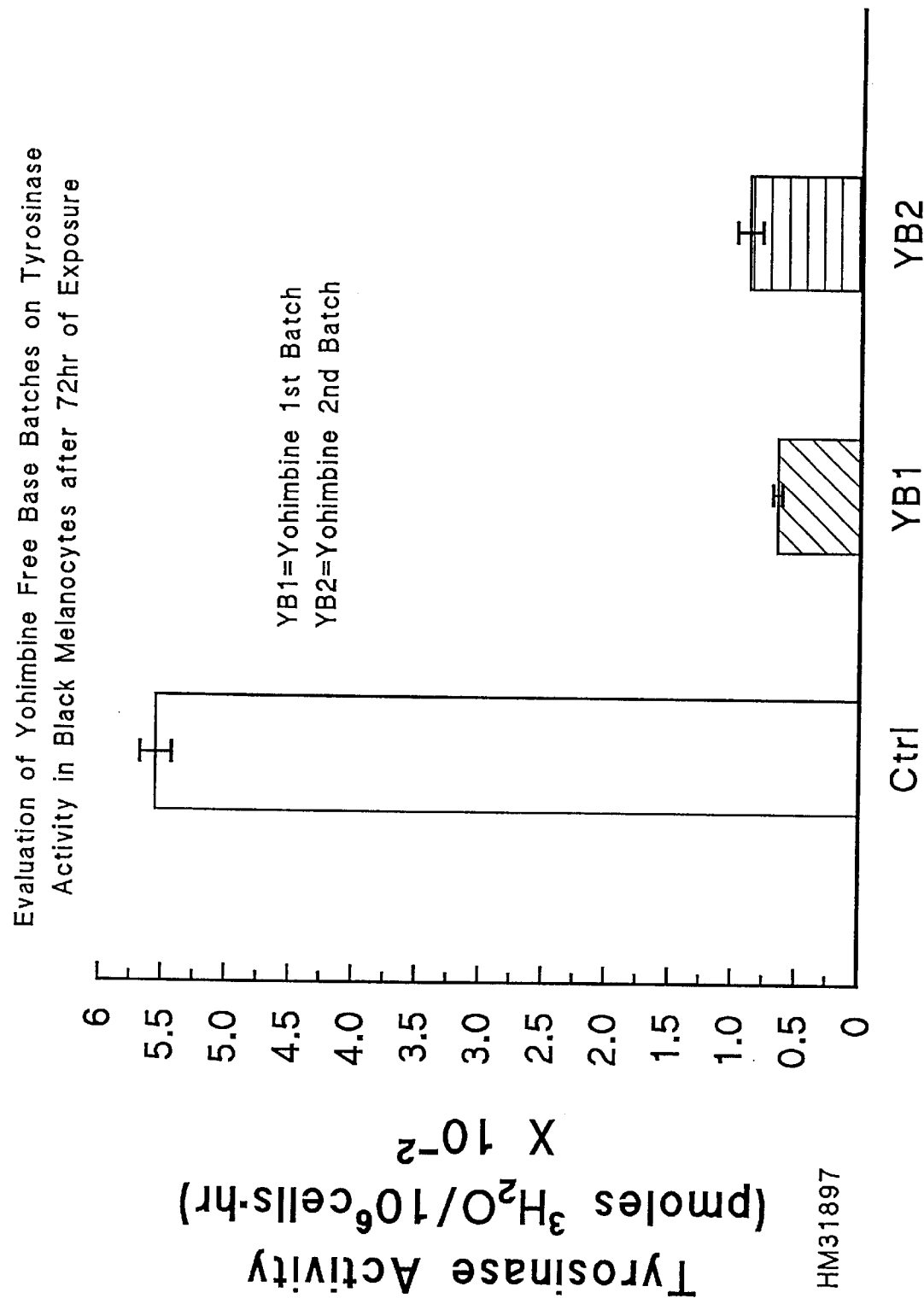
FIG. 2 is a graph showing the effect of free base yohimbine on tyrosinase activity in melanocytes.

FIG. 2 shows the same inhibitory effect of separate batches of yohimbine prepared as a free base (dissolved in ethanol) at a concentration of 100 μM. The degree of inhibition is similar to that shown in FIG. 1.

Figure 3:
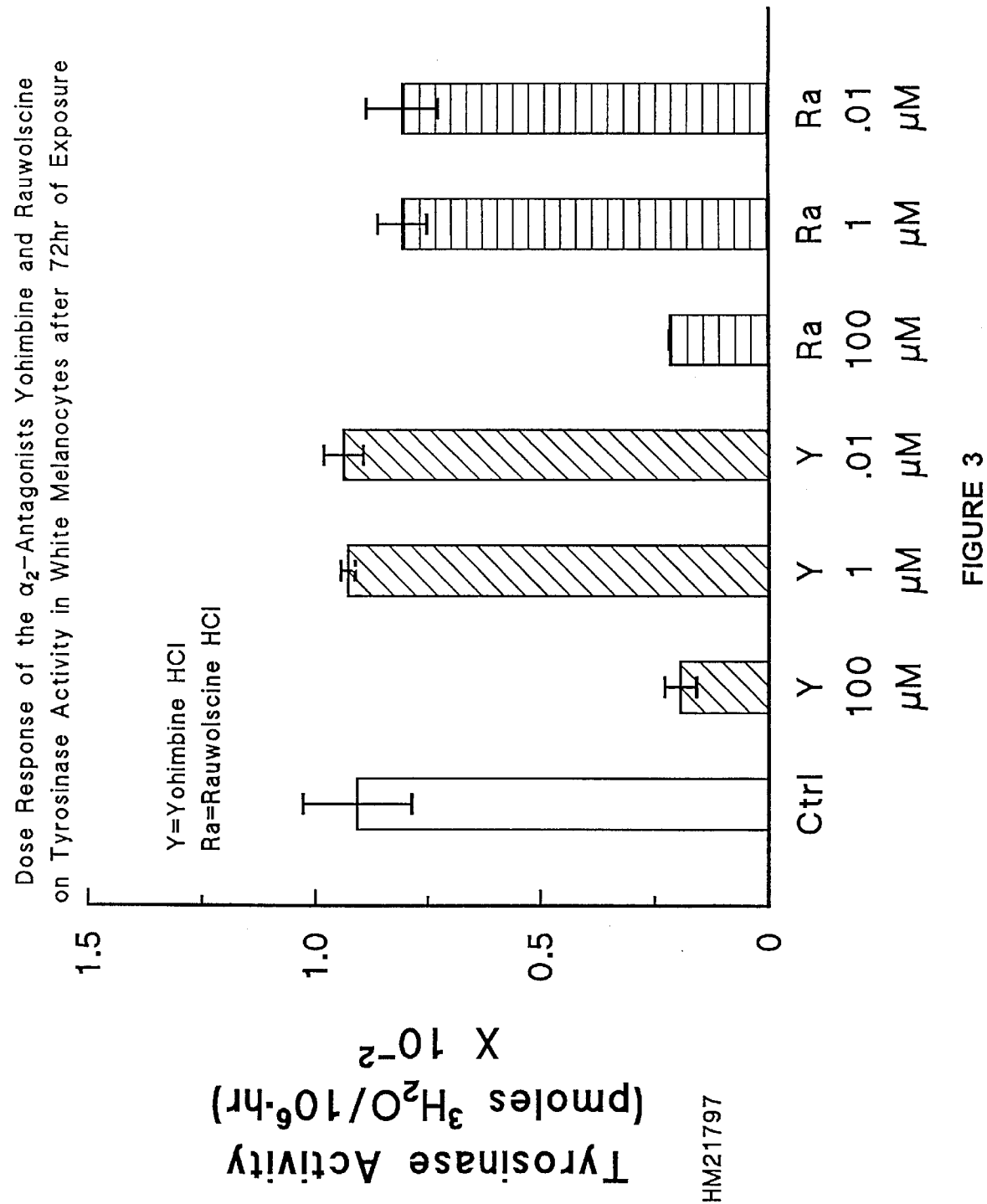
FIG. 3 is a graph showing the comparative effects of yohimbine and the yohimbine stereoisomer rauwolscine on tyrosinase activity in melanocytes.

FIG. 3 shows a similar inhibitory effect, at a similar degree, using the yohimbine stereoisomer rauwolscine (α-yohimbine) in white melanocytes (strain W442) incubated for 72 hours.

Figure 4:
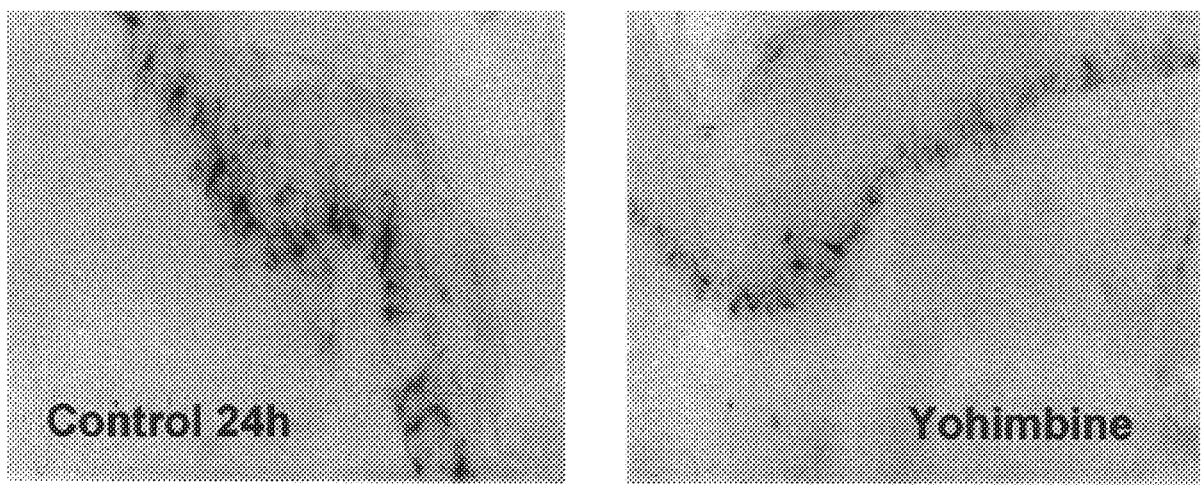
FIG. 4 is a photograph and graph showing the lightening effect of yohimbine on a human skin culture.
Figure 4:
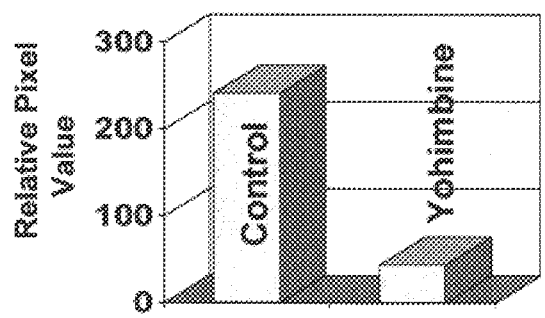

FIG. 4 shows a pixel graph and a photograph of histological slides of black foreskins cultured as described above which have been incubated for 24 hours with yohimbine (100 μM) and without yohimbine (the control) in the growth medium. The skin treated with yohimbine is clearly less densely stained than the untreated foreskin. In terms of relative pixel value, the control foreskin is approximately 5X darker than the foreskin which was treated with yohimbine.

Figure 5:
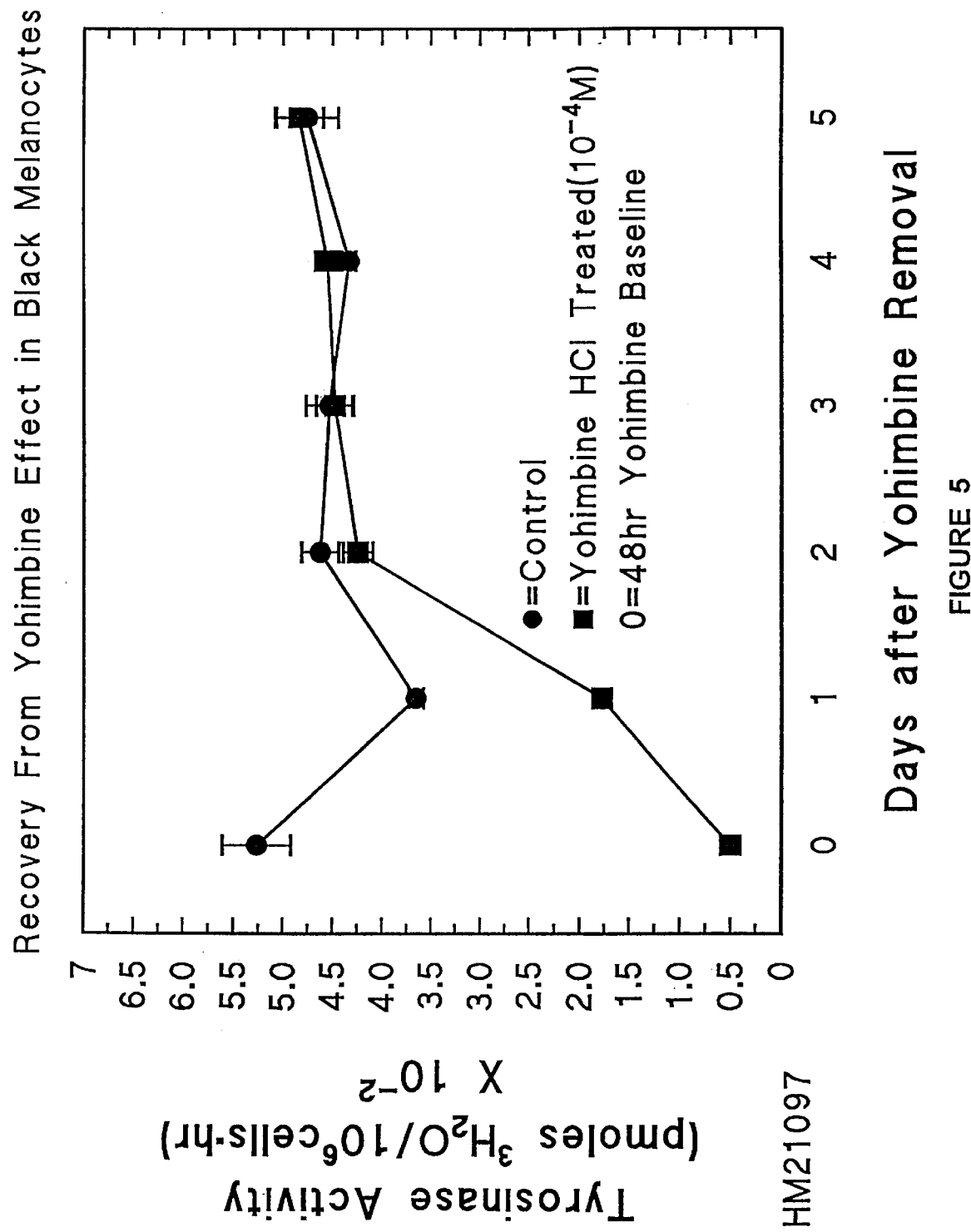
FIG. 5 is a graph showing the recovery of tyrosinase activity in human melanocyte cell culture after removal of yohimbine from the culture medium.

FIG. 5 shows the recovery effect in black melanocytes (strain B417). Melanocytes which had been treated with yohimbine (100 μM) were provided with nutrient media without yohimbine. Within 48 hours, the melanin production in the treated melanocytes was back to the same level as the melanocytes exposed to the medium without yohimbine. The results demonstrate that the effect of yohimbine is reversible and that the yohimbine must be repeatedly applied to maintain the inhibitory effect.

Figure 6:
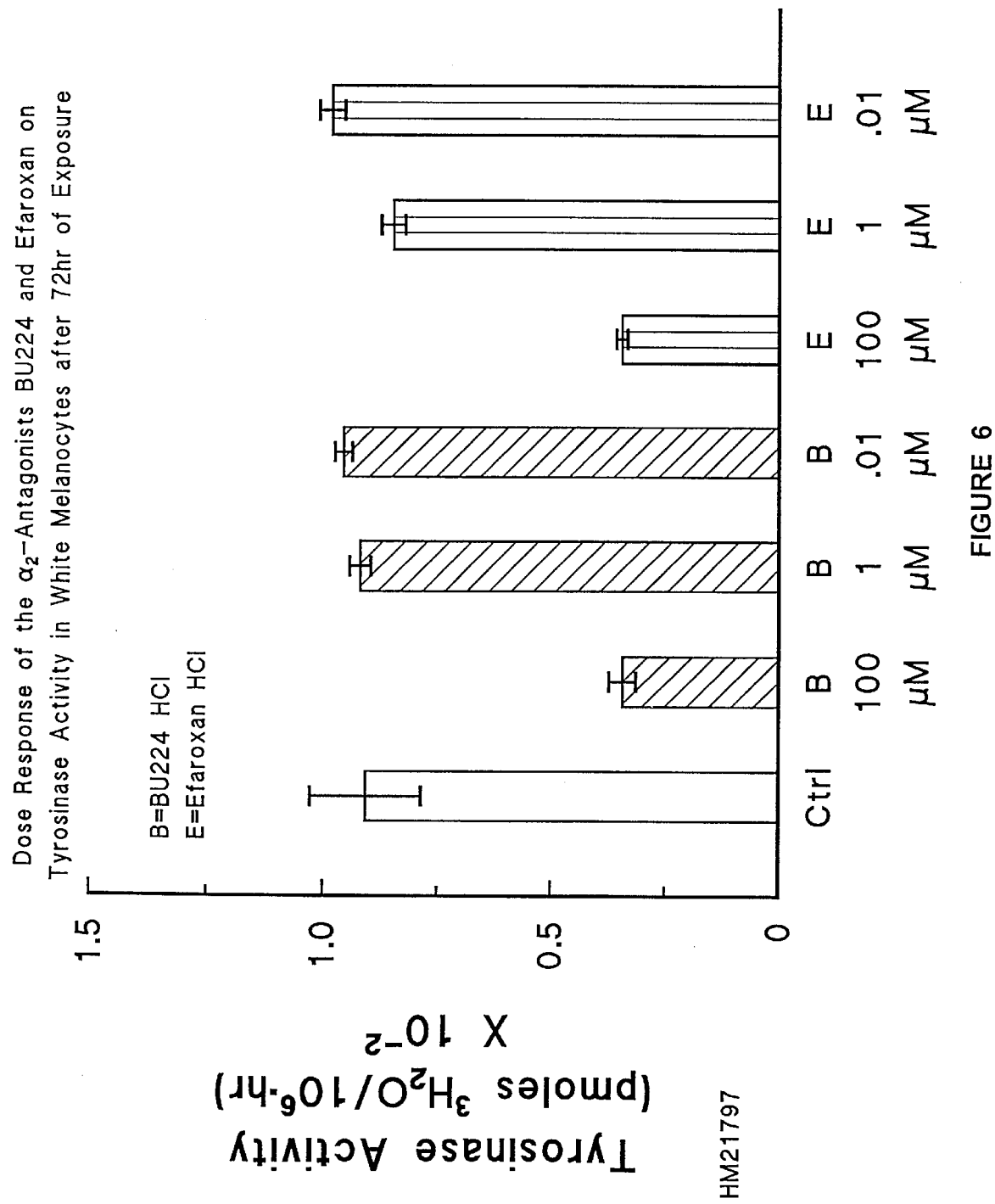
FIG. 6 is a graph showing the effects of $\alpha_{-2}$-antagonists BU224 and efaroxan on tyrosinase activity in another human melanocyte cell culture.

FIG. 6 shows an inhibitory effect of two effective $\alpha_2$-antagonists BU224 and efaroxan on white melanocytes (strain W442) treated for 72 hours. BU224 and efaroxan at concentrations of 100 μM inhibited melanogenesis.

Figure 7:
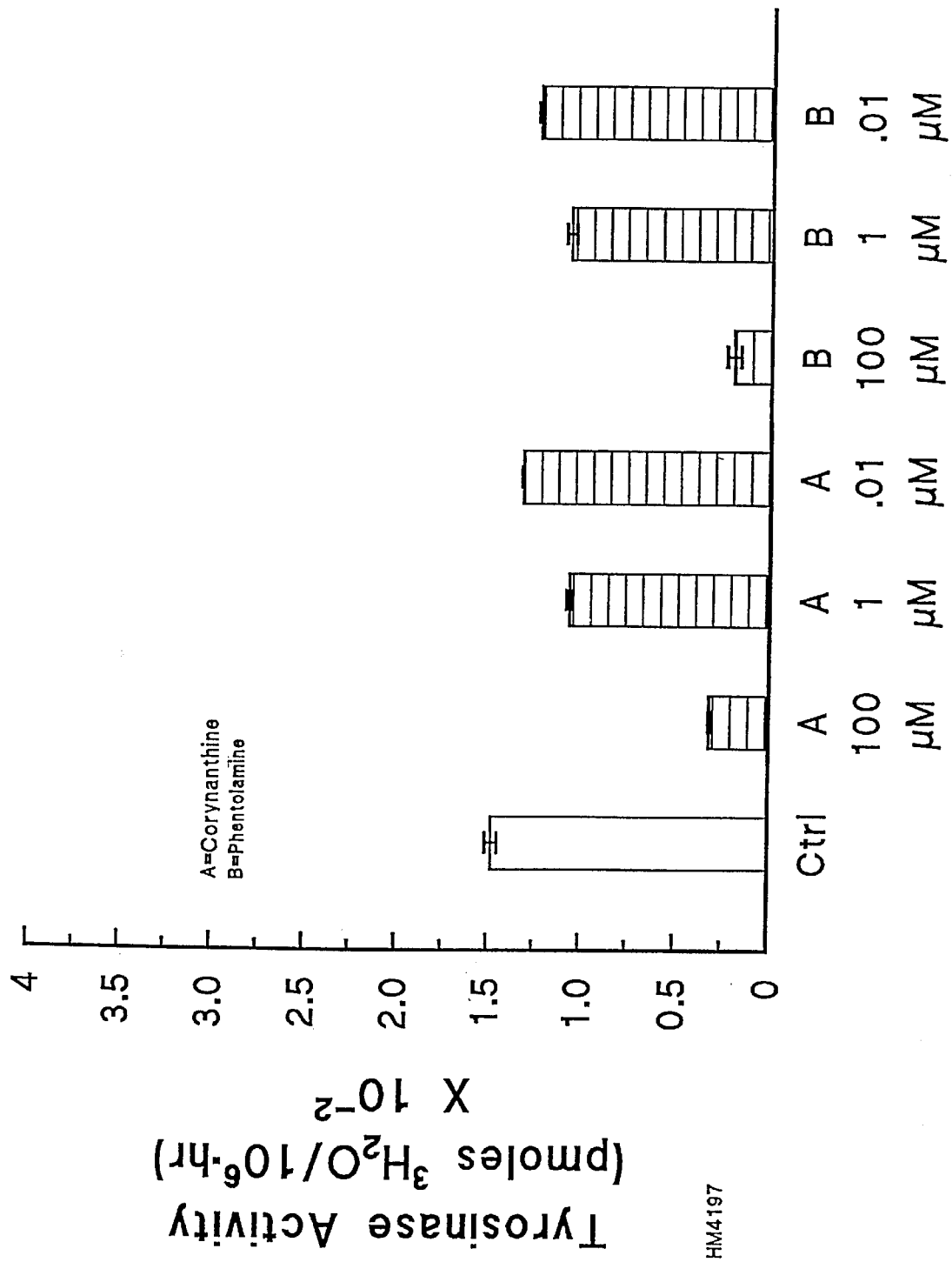
FIG. 7 is a graph showing the effects of phentolamine and the yohimbine stereoisomer corynanthine on tyrosinase activity in another human melanocyte cell culture.

FIG. 7 shows an inhibitory effect of the α-antagonist phentolamine and of the yohimbine stereoisomer corynanthine on white melanocytes (strain W424) treated for 72 hours. Phentolamine and corynanthine at 100 μM inhibited melanogenesis.

Figure 8:
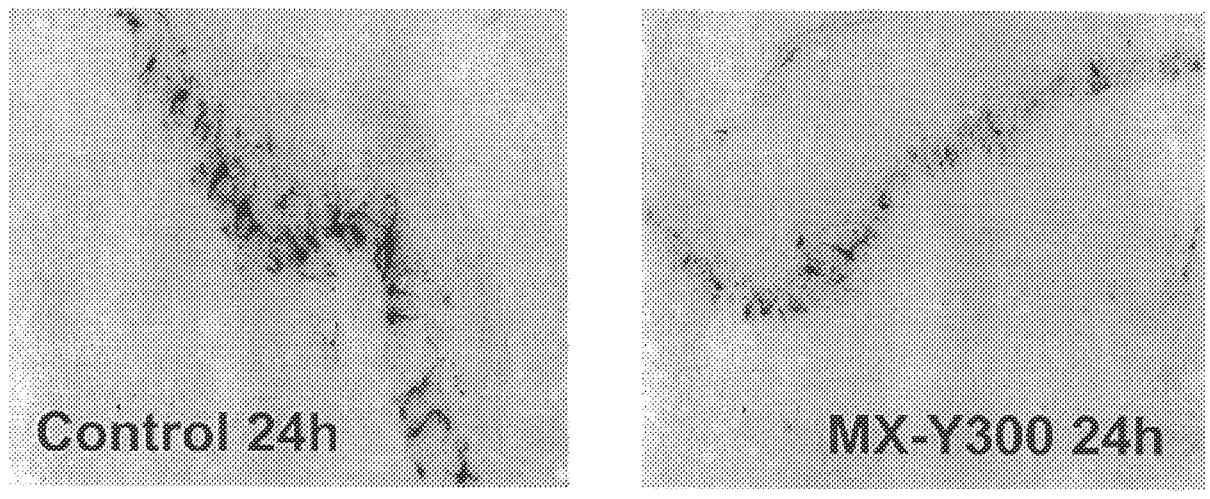
FIG. 8 is a photograph and graph showing the depigmentizing effect of natural Johimbe bark extract on a human skin culture.
Figure 8:
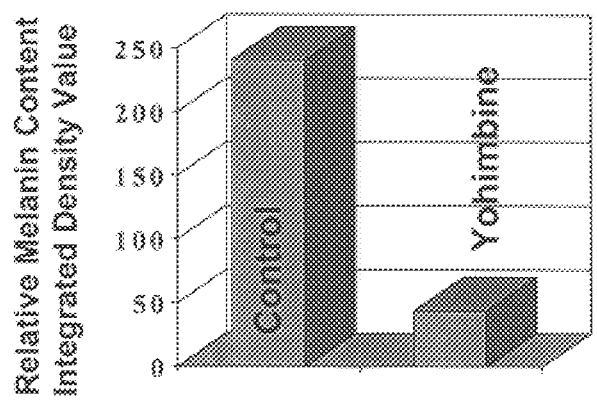

FIG. 8 shows a pixel graph and a photograph of histological slides of black foreskins cultured as described above, which were incubated for 24 hours with and without a yohimbine-containing extract of Johimbe bark (extraction process described below). The skin treated with the yohimbine-containing extract of Johimbe bark is clearly less densely stained than the ethanol control. In terms of relative density, the control foreskin is approximately 4X darker than foreskin which was treated with the extract.

Johimbe Bark Extraction Method

Ten g of Johimbe (Yohimbe) bark (obtainable commercially, for example, from the Gaia Herb Co.) was milled in a coffee mill for 20 seconds to reduce bark to fine sediment, and then 100 ml of water was added. The mixture was stirred for 1 hour at room temperature in a 250 ml Erlenmeyer flask and then centrifuged at 5000 xg for 20 minutes. The supernatant was discarded and the sediment containing yohimbine was resuspended in 100 ml of ethanol. This mixture was sonicated briefly and then stirred for 5 hours at room temperature to further extract the yohimbine from the bark. After stirring, the mixture was again centrifuged and the supernatant saved. The pellet was discarded. The ethanol supernatant was evaporated under nitrogen gas until the volume had been reduced to 16 ml. This resulted in an ethanol solution which contained approximately 100 microMolar yohimbine. The concentration of yohimbine in the extract will vary depending on the bark source and technique used.

It will be understood by a person of ordinary skill in the art that the extraction method described herein is but one of many suitable methods which may be used to obtain an extract of yohimbine and all such methods are contemplated as being within the scope of the present invention as claimed herein.

These data show that yohimbine and various derivatives and stereoisomers thereof and certain effective $\alpha_2$-antagonists are effective in decreasing tyrosinase activity in human melanocyte cells thereby inhibiting melanogenesis leading to skin lightening.

Changes may be made in the construction and the operation of the various compositions described herein or in the steps or the sequence of steps of the methods described herein without departing from the spirit and scope of the invention as defined in the following claims.

What is claimed is:

1. A composition for causing lightening of the epidermis comprising:
    an extract of Johimbe tree bark; and
    a cosmetically acceptable topical vehicle or carrier which is effective in enabling penetration of an active agent in the extract through the stratum corneum into the layer of the epidermis comprising melanocytes.

2. The composition of claim 1 comprising an alcohol.

3. The composition of claim 1 comprising a penetration enhancer.

4. The composition of claim 1 wherein the extract comprises 0.01% to 80% by weight of the composition.

5. A composition for causing lightening of the epidermis comprising:
    an extract of a natural source comprising yohimbine or a stereoisomer or salt thereof; and
    a cosmetically acceptable topical vehicle or carrier which is effective in enabling penetration of the yohimbine, stereoisomer or salt thereof through the stratum corneum into the layer of the epidermis comprising melanocytes.

6. The composition of claim 5 wherein the extract is an extract of Johimbe bark.

7. The composition of claim 5 comprising an alcohol.

8. The composition of claim 5 comprising a penetration enhancer.

9. The composition of claim 5 wherein the extract comprises 0.01% to 80% by weight of the composition.

10. The composition of claim 1 further comprising a sunscreen agent.

11. The composition of claim 1 further comprising a thickener.

12. The composition of claim 1 further comprising a film former.

13. The composition of claim 5 further comprising a sunscreen agent.

14. The composition of claim 5 further comprising a thickener.

15. The composition of claim 5 further comprising a film former.

* * * * *